United States Patent [19]

Tsujiuchi et al.

[11] 4,147,052
[45] Apr. 3, 1979

[54] HARDNESS TESTER

[75] Inventors: Junpei Tsujiuchi; Toshio Honda, both of Kanagawa; Hiroshi Okuda, Tokyo, all of Japan

[73] Assignee: Kabushiki Kaisha Daini Seikosha, Japan

[21] Appl. No.: 825,398

[22] Filed: Aug. 17, 1977

[30] Foreign Application Priority Data

Aug. 19, 1976 [JP] Japan .................................. 51-99051
Aug. 19, 1976 [JP] Japan .................................. 51-99050

[51] Int. Cl.² ............................................. G01N 3/42
[52] U.S. Cl. .................................................... 73/81
[58] Field of Search ................................ 73/81, 83, 82

[56] References Cited

U.S. PATENT DOCUMENTS

| 2,713,259 | 7/1955 | Grodzinski et al. | 73/81 |
| 3,737,856 | 6/1973 | Lehrer et al. | 356/165 |
| 3,739,630 | 6/1973 | Llop | 73/81 |
| 3,822,946 | 7/1974 | Rynkowski | 73/81 |

Primary Examiner—Anthony V. Ciarlante
Attorney, Agent, or Firm—Robert E. Burns; Emmanuel J. Lobato; Bruce L. Adams

[57] ABSTRACT

A hardness tester has an image sensor and a detecting system. The image sensor has aligned plurality photoelectric sensor elements on an image plane on which a bright and dark image of an indentation is formed through an optical system. The detecting system detects the diagonal length of the indentation by using the differences in amplitude of the output signals developed by the sensor elements in the vicinity of the ends of the indentation image.

6 Claims, 11 Drawing Figures

FIG. 4
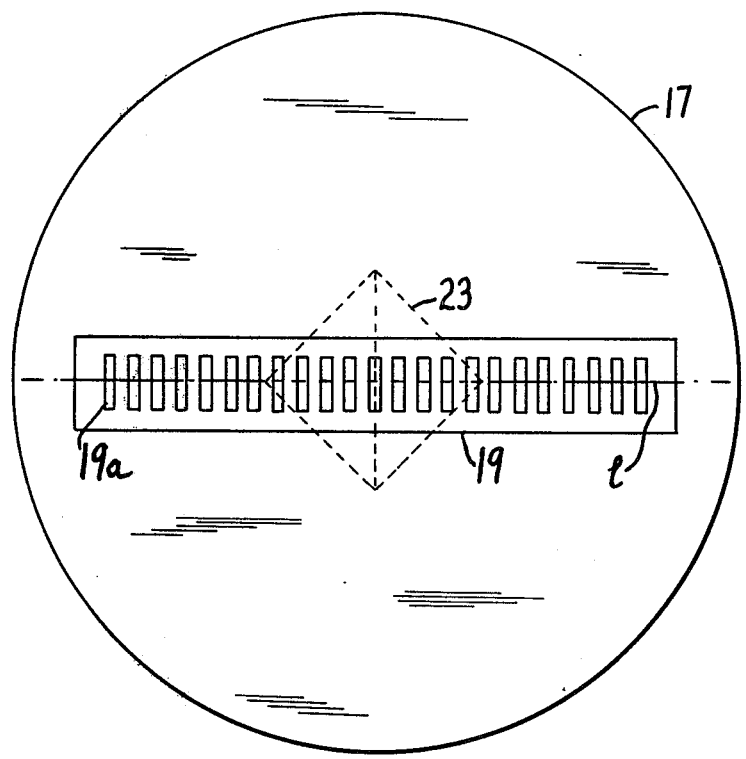
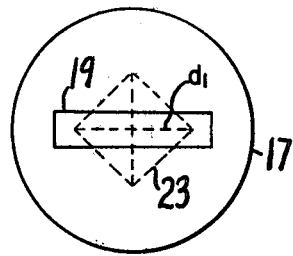
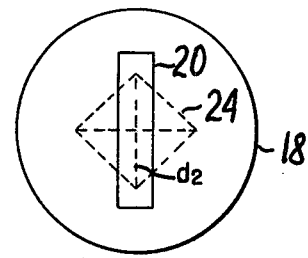
FIG. 5a    FIG. 5b

HARDNESS TESTER

BACKGROUND OF THE INVENTION

This invention relates to a hardness tester which it makes possible to measure automatically hardness of specimens by using an image sensor.

The Vicker's hardness test is widely adopted as the typical one of the hardness tests for metallic material or the like. In the Vicker's test a load is applied slowly to the testing surface of specimen 2 using a quadrangular pyramid shaped diamond penetrator 1 (refer to FIG. 1a), having face to face angle $\theta = 136$ degree thereof, and by this loading operation produces a dent 3 (hereafter called indentation) on the said surface, and the hardness value of the said specimen is defined as the quotient of the applied load divided by the surface area of the permanent indentation which remains after removing the load. That is, whereupon the applied load is P kg., and the diagonal length d mm of the said indentation 3 is measured, the Vicker's hardness HV can be indicated as follows:

$$HV = 2P/d^2 \sin 68° = 1.854 \ P/d^2 \ Kg/mm^2$$

Among this Vicker's hardness test, a microvicker's tester or the like has been widely used in the past, and the measuring method thereof is that after giving a load to a specimen 2 by a diamond penetrator 1 of the loading mechanism of said tester and forming an indentation 3, the said diamond penetrator 1 is replaced with a measuring microscope using a resolver thereof without moving the specimen 2. Then, as shown in FIG. 2a, the diagonal edge points 3a, 3b of said indentation 3 formed on the specimen surface coincides with the edges of every reference lines 4a, 4b engraved on a resolver glass placed at the focal plane of the eyepiece in said microscope within the visual range thereof by the given operation and thus the diagonal length d of said indentation 3 is measured. But when the operator coincides the edges 3a, 3b of said indentation 3 with the edges of the every reference lines 4a, 4b within the visual range of said microscope, the coinciding position varies at every measuring operation due to the shape of said reference lines, the size of said indentation 3 and the physical condition of the operator.

Further, deviations appear at the coinciding positions of the edges of said reference lines 4a and 4b with edge points 3a and 3b of said indentation 3 due to personal error as shown in FIGS. 2b and 2c. If more than two operators measure the same indentation, the mutual difference appears naturally due to personal errors. As mentioned above, as for the Vicker's hardness tester due to such conventional visual measurement, the coinciding positions of the indentation edges 3a and 3b with the edges of the reference lines 4a and 4b could not be defined constant on account of the parallax of the operator himself or between the operators, or on account of the physical condition of the operator, therefore, therre have been defects which caused considerable amount of errors of the measured hardness value.

SUMMARY OF THE INVENTION

The present invention relates to a hardness tester to detect hardness of a specimen by means of forming a polygonal pyramid shaped indentation using a penetrator and by means of measuring the diagonal length of said indentation, characterised by an image sensor having arranged multiple photo-electric conversion elements on an imaging plane portion on which a bright and dark image of said indentation is formed through an optical means, and a detecting means for detecting the diagonal length of said indentation according to the output of said image sensor.

An object of the invention is to provide an improved hardness tester to make an accurate hardness test by decreasing the personal errors caused by visual measurement.

Another object of the invention is to provide a hardness tester which reduces the operator's working burdens.

A further object of the invention is to provide an improved hardness tester which measures photo-electrically the diagonal length of an indentation formed on a specimen.

BRIEF DESCRIPTION OF THE DRAWINGS

FIG. 4 is a plan view showing the relation between the indentation image on an imaging plane and a image sensor.

FIG. 5a is a plan view showing the imaging plane having an image sensor arranged in the X-direction.

FIG. 5b is a plan view showing the imaging plane having an image sensor arranged in the Y-direction.

DESCRIPTION OF THE PREFERRED EMBODIMENT

Hereafter, one of the embodiments of this invention applied to a Vicker's hardness tester will be described in detail in conjunction with the drawings.

Figure 1A:
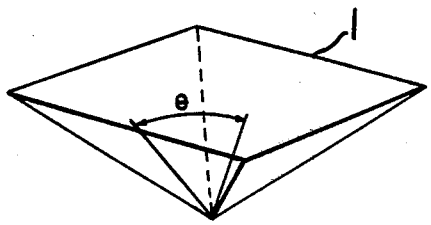
FIG. 1a is a perspective view of a portion of a diamond penetrator.
Figure 1B:
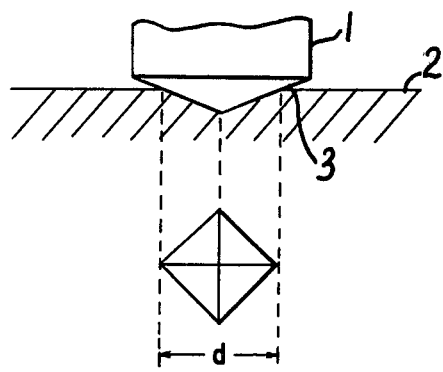
FIG. 1b is an elevational and a plan view showing the relation between a penetrator and a specimen.
Figure 2A:
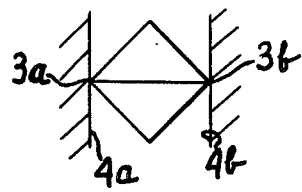
FIGS. 2a, b and c are views showing the relation between reference lines and an indentation image.
Figure 2B:
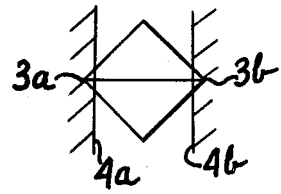
Figure 2C:
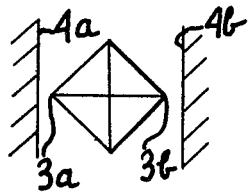
Figure 3:
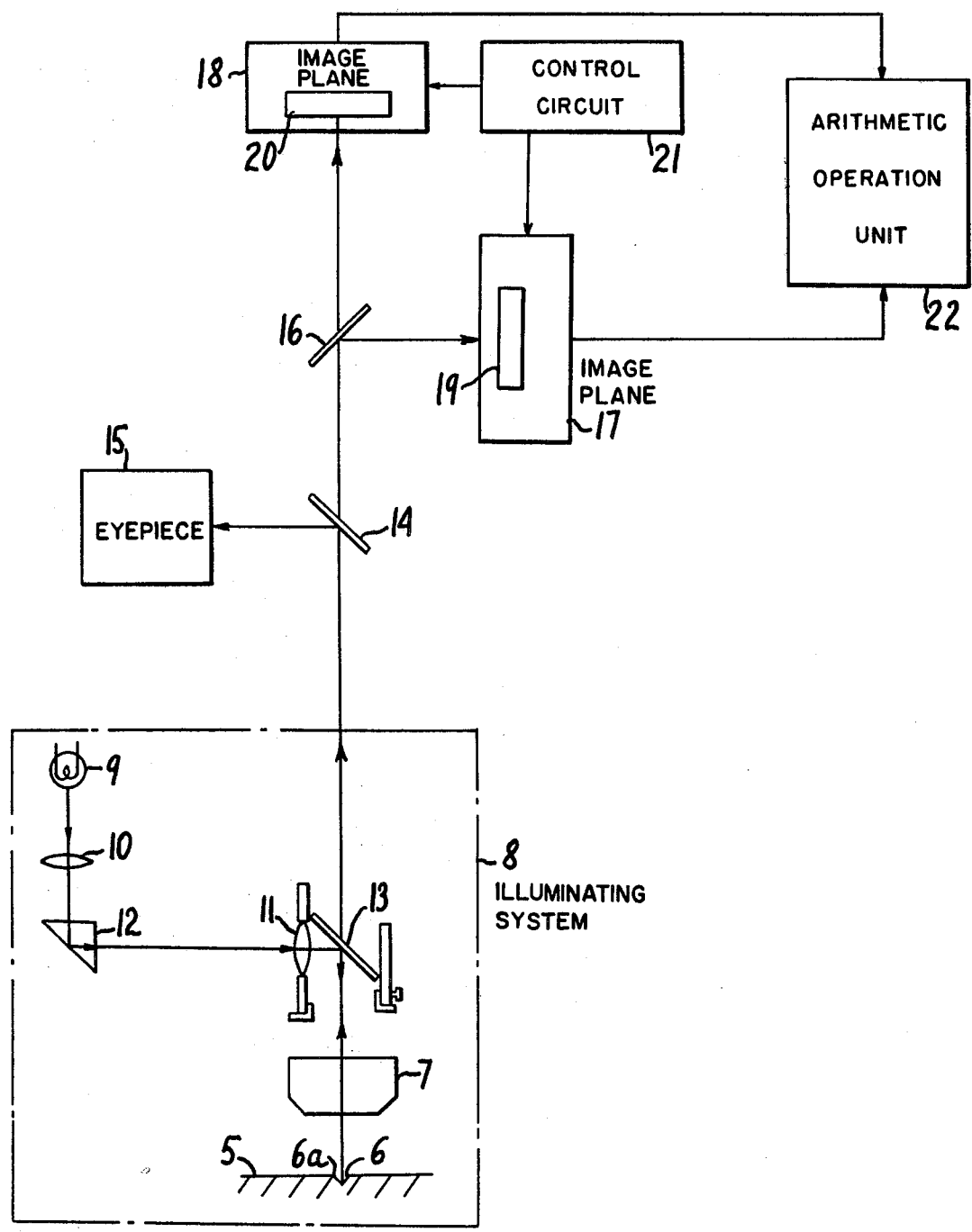
FIG. 3 is a block diagram showing the principle of the hardness tester according to the present invention.

FIG. 3 is a block diagram illustrating a Vicker's hardness tester according to this invention. In FIG. 3, 5 is a specimen such as metallic material or the like on the surface of which a quadrangular pyramid shaped indentation 6 is formed by pressing a diamond penetrator thereon through the loading mechanism of a hardness tester. The specimen 5 is set directly under an objective 7 to obtain a magnified image of the indentation b. 8 is an illuminating system to produce a distinct bright and dark difference or silhouette between the indentation portion and the surrounding portion thereof and is comprised of a tungstem lamp 9, lenses 10 and 11, a prism 12, a beam splitter 13. So the light radiated from the tungsten lamp 9 illuminates the indentation portion formed on the specimen surface and the surrounding portion thereof, passing through the lens 10, the prism 12 and the lens 11, reflecting off the beam splitter 13 and passing through the objective 7. And then, the reflected light from the said indentation 6 and the said surrounding portion 6a thereof is introduced to a beam splitter 14 passing again through the objective 7 and the beam splitter 13, and the light reflected with this beam splitter 14 is introduced to an eye piece 15. The ray passed through the said beam splitter 14 is introduced to a next beam splitter 16 and the ray reflected off the beam splitter 16 is introduced to a first image plane 17 and the ray passed through the said beam splitter 16 is introduced to a second image plane 18. Accordingly, the indentation images distinctly divided into the dark images of the inclined surfaces of the indentation 6 and the bright images of the surrounding portion 6a thereof are respectively projected on the image planes 17 and 18 and further can be observed with the eyepiece 15.

Numerals 19 and 20 are image sensors placed on the said image planes 17 and 18 respectively and comprise arrays of photo-diodes or charge coupled device or the like. On the photo-sensitive area of the image sensor, there are linearly arranged multiple elements 19a having narrow breadth-type shape with a predetermined interval in the breadth direction as shown in the FIG. 4. This image sensor 19 is placed on the said image plane 17 so as to project the bright and dark portion of said indentation pattern and the center line 1 (an imaginary line connecting the center of each element as shown in FIG. 4) is previously positioned aligned with the direction of said reference lines engraved on the glass placed on the focal plane of said eyepiece 15. That is, just then the operator fixes the position of the diagonal line of indentation image 23 with the said reference lines by looking into the eyepiece 15. At the fist image plane 17, the diagonal line $d_1$ of X-direction of said indentation image 23 projected thereon coincides with said center line 1 of the image sensor 19 (refer to Fig. 5a). At the second imaging plane portion 18, the diagonal line $d_2$ of Y-direction of said indentation image 24 projected thereon coincides with said center line 1 of the image sensor 20 (refer to FIG. 5b). The image sensors 19 and 20 are controlled by a control circuit 21 together. The outputs corresponding to light intensity incident on each element of the photosensitive areas of the image sensors 19 and 20 is applied to an arithmetic operation unit 22 synchronously with a clock signal in serial order. These video-outputs i.e., the output signals corresponding to the outputs of the diagonal line $d_l$ of X-direction developed by the image sensor 19 and the output signals of the $d_2$ of Y-direction developed by the image sensor 20, are applied to the arithmetic operation unit 22, such as a minicomputer, which performs arithmetic operation as discussed below.

Figure 6:
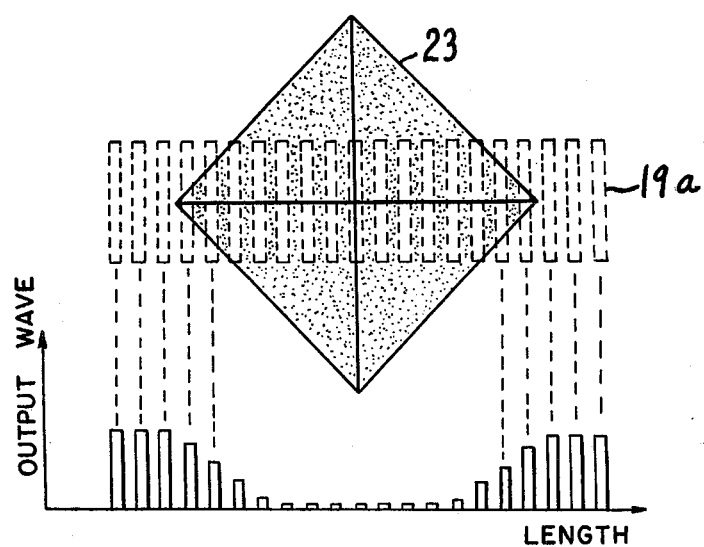
FIG. 6 is a wave form chart of the output of the image sensor corresponding to the bright and dark portions of the indentation image.
Figure 7:
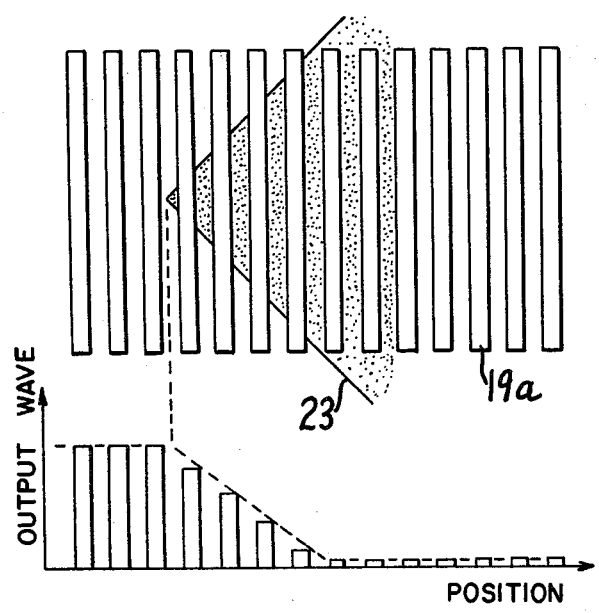
FIG. 7 is a wave form chart of the output of the image sensor corresponding to the bright and dark portions of the corner vicinity of the indentation image.

In the above construction, the indentation images produced by the illumination system 8, in the case of an image projected on the first image plane 17 will be described, whereupon the outputs of every element 19a on the photosensitive area of the image sensor 19 form an output having a waveform corresponding to the brightness and darkness on the image plane, as shown in FIG. 6. That is, the amplitude of the output of every element 19a located totally in the indentation image 23 formed in the darkness is low and the amplitude of every element 19a deviated from the indentation image 23 high. And the amplitude of the output of the every element 19a located in the vicinity of the corner of the indentation image 23 has a value between the above low and high values.

The outputs are classified into two values of brightness and darkness with a predetermined threshold value and the prescribed arithmetic operation is performed, so that the breadth of said dark portion, i.e., the diagonal length of the indentation can be normally otained. And further, if the diagonal length is more precisely required, the inclination of the output waves of every element 19a located in the corner vicinity of the indentation image 23 formed on the image plane 17 is utilized. That is, the wave shapes of the output of every element 19a located in the said corner vicinity are photo-electrically converted to the equivalent values corresponding to the middle ones between the dark indentation portion 23 and the bright surrounding one thereof. Accordingly, the height of output waves of every element 19a located in the corner vicinity of the indentation image 23 produces an inclination. Then, for an instance, some of the elements 19a which forms an inclination of output wave are properly selected and the prescribed arithmetic operation on the inclination are performed, whereupon the terminal points of the inclination, i.e., the end points of the diagonal of the indentation image 23 can be determined so that the diagonal length $d_1$ of said indentation image 23 in X-direction can be very precisely obtained. Furthermore, in the case of image 24 projected on the second image plane 18, the diagongal length $d_2$ of said indentation image 24 in Y-direction can be obtained by the same processes as mentioned above with respect to the X-direction. Therefore, in case the corner top points of the indentation image 18 or 19 are broken off for some reason or the corner top points accidentally fall on the interval portions between elements 19a, the diagonal length $d_1$ or $d_2$ of said indentation image 23 or 24 can be precisely calculated.

In the above embodiment, the setting positions of the image sensors on the every image planes must coincide with the diagonal lines of the indentation images, but this invention is not limited to such coincidence conditions. For instance, in case the shape of indentation becomes unequal or unsymmetrical by partial unevenness of hardness of specimen such as metallic material or the like, the setting positions of the image sensors on every image plane may be properly varied to optimum positions for measurement.

As described hereinbefore, the hardness tester according to this invention is constructed to divide optically the indentation image into plural sections and to project said images on respective image planes at which respective band-shaped image sensors are provided. Each image sensor measures one transverse dimension of the indentation. The measuring errors of said indentation are extremely small and high precision hardness testing can be performed.

Furthermore, this invention is effective to reduce personal errors and mutual difference between operators which have existed in the conventional Vicker's hardness tester due to visual measurement and it is also able to reduce operator's working burdens.

What is claimed is:

1. A hardness tester for determining hardness of a specimen, comprising: indenting means for forming a polygonal pyramidal indentation in a surface of a speciman; imaging means for forming an optical silhouette image of the speciman surface indentation; a solid state image sensor comprised of a plurality of photoelectric sensor elements, each photoelectric sensor element having a narrow elongated photoresponsive area and said plurality of photoelectric sensor elements being relatively positioned with their respective photoresponsive areas positioned along a straight line defining a major axis of said solid state image sensor and with the lengths of their respective photoresponsive areas transverse to the major axis of said solid state image sensor, and said solid state image sensor positioned with the optical image of the specimen surface indentation incident on the photoresponsive areas of said photoelectric sensor elements comprising said solid state image sensor with said photoelectric sensor elements developing respective electrical output signals each having an amplitude representing the intensity of the optical image incident thereon; and detecting means responsive to the differences in amplitude of the electrical output signals developed by said photoelectric sensor elements in the vicinity of the ends of the speciman surface indentation image for detectingthe diagonal length of the speciman surface indentation image along the major axis of said solid state image sensor.

2. A hardness tester as claimed in claim 1, where said indenting means forms a quadrangular pyramidal indentation.

3. A hardness tester as claimed in claim 1, wherein said imaging means forms a plurality of specimen surface indentation images, and further comprising a solid state image sensor having the same structure as the first-mentioned solid state image sensor for sensing each of the specimen surface indentation images.

4. A hardness tester as claimed in claim 3, wherein the major axis of each solid state image sensor is oriented along a different diagonal of the respective specimen surface indentation image incident thereon.

5. A hardness tester as claimed in claim 4, wherein said indenting means forms a quadrangular pyradmidal indentation, and said imaging means forms two images of the specimen surface indentation.

6. A hardness tester as claimed in claim 1, wherein the respective photoresponsive areas of said plurality of photoelectric sensor elements are rectangular and of the same size, and are disposed equi-spaced along the major axis of said solid state image sensor.

* * * * *